(12) United States Patent
Kebebew (10) Patent No.: US 7,901,888 B2
(45) Date of Patent: Mar. 8, 2011

(54) MULTIGENE DIAGNOSTIC ASSAY FOR MALIGNANT THYROID NEOPLASM

(75) Inventor: Electron Kebebew, Novato, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/117,500

(22) Filed: May 8, 2008

(65) Prior Publication Data

US 2008/0280302 A1 Nov. 13, 2008

Related U.S. Application Data

(60) Provisional application No. 60/916,873, filed on May 9, 2007.

(51) Int. Cl.
*C12Q 1/68* (2006.01)

(52) U.S. Cl. ......................................................... 435/6

(58) Field of Classification Search ........................ None
See application file for complete search history.

(56) References Cited

OTHER PUBLICATIONS

Kebebew et al I (Cancer, Jun. 2006, 106:2592-2597).*
Kebebew et al II (Surgery, Dec. 2005, 138:1102-1110, IDS).*
Kebebew et al III (Annals of Surgery, Sep. 2005, 242:353-363).*
Kebebew, M.D., Electron, et al. "Diagnostic and Extent of Disease Multigene Assay for Malignant Thyroid Neoplasm," American Cancer Society, 2006, pp. 2592-2597.
Kebebew, M.D., Electron, et al. "Predictors of Single-Gland vs Multigland Parathyroid Disease in Primary Hyperparathyroidism; A simple and accurate Scoring Model," American Medical Association, 2006, pp. 777-782.
Kebebew, M.D., Electron, et al. "Diagnostic and value of angiogenesis-modulating genes in malignant thyroid neoplasms," Surgery, 2005, vol. 138, No. 6, pp. 1102-1110.
Kebebew, M.D., Electron, et al. "Diagnostic and Prognostic Value of Cell-cycle Regulatory Genes in Malignant Thyroid Neoplasms," World J. Surg., 2006, vol. 30, pp. 767-774.

* cited by examiner

*Primary Examiner* — Laura B Goddard
(74) *Attorney, Agent, or Firm* — Morgan, Lewis & Bockius LLP; Annette S. Parent (57) ABSTRACT

The present invention provides methods for diagnosing, providing a prognosis, and staging thyroid cancer, using panels of molecular markers that are differentially expressed in thyroid cancer. Also provided are methods to identify compounds that are useful for the treatment or prevention of thyroid cancer.

6 Claims, 4 Drawing Sheets

MULTIGENE DIAGNOSTIC ASSAY FOR MALIGNANT THYROID NEOPLASM

CROSS-REFERENCES TO RELATED APPLICATIONS

This application claims priority to provisional application, U.S. Ser. No. 60/916,873, filed May 9, 2007, the contents of which are herein incorporated by reference in their entirety into this application.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Thyroid cancer is the fastest growing cancer diagnosis in the U.S. with approximately 30,000 new cases of thyroid cancer occurring each year. Thyroid cancer occurs three-times more often in women than in men and is most common after age 30, although it can occur in any age group. Its aggressiveness increases significantly in older patients. Since the advent of high-resolution ultra-sonography and other sensitive imaging techniques, the number of patients with thyroid nodules requiring clinical evaluation has increased dramatically and approaches 50% of the U.S. population.

Fine needle aspiration (FNA) biopsy has reduced the number of diagnostic thyroidectomies for benign thyroid neoplasms, (Greaves et al,. *Cancer.* 90(6):335-341 (2000); Baloch, Z. W. et al., *Diagn Cytopathol.* 26(1):41-44 (2002); Gharib, H. et al., *Ann Intern Med.* 118(4):282-289 (1993); Cersosimo, E. et al., *Mayo Clin Proc.* 68(4):343-348 (1993); Gharib, H. et al., *Clin Lab Med.* 13(3):699-709 (1993); Hooft, L. et al., *Thyroid.* 14(4):287-293 (2004)) but may be nondiagnostic or show indeterminate or suspicious cytologic features in 20% to 30% of all thyroid nodules (Greaves et al. *Cancer.* 90(6):335-341 (2000); Baloch, Z. W. et al., *Diagn Cytopathol.* 26(1):41-44 (2002); Gharib, H. et al., *Ann Intern Med.* 118(4):282-289 (1993)). Because the risk of malignancy is anywhere from 5% to 30% for follicular tumors and about 50% in nodules suspicious for papillary thyroid cancer, diagnostic thyroidectomy is usually recommended. Unfortunately, no preoperative clinical or imaging factors can reliably determine which patients with suspicious, nondiagnostic or indeterminate FNA cytologic findings should undergo thyroidectomy (Tuttle, R. M. et al., *Thyroid.* 8(5):377-383 (1998); Basu, D. et al., *Diagn Cytopathol.* 8(1):23-27 (1992); Eldar, S. et al., *Histopathology.* 34(5):453-461 (1999); Tyler, D. S. et al., *Surgery.* 116(6):1054-1060 (1994)).

Many prognostic scoring systems (TNM, AMES, AGES, MACIS, EORTC) have been used to estimate disease-free survival and cause-specific mortality in patients with thyroid cancer (Kebebew, E. et al., *World J Surg.* 24(8):942-951 (2000); Brierley, J. D. et al., *Cancer.* 79(12):2414-2423 (1997); Sanders, L. E. et al., *Arch Surg.* 133(4):419-425 (1998); Dean, D. S. et al., *Cancer Control.* 7(3):229-239 (2000)). The main use of these risk classification systems is to identify patients with a poor prognosis, to ensure that they receive additional treatment such as radioiodine ablation, and get closer follow-up monitoring (Mazzaferri, E. L. et al., *J Clin Endocrinol Metab.* 88(4):1433-1441 (2003)). Unfortunately, none of these staging systems include data that are completely available preoperatively to guide the extent of initial surgical resection necessary (Kebebew, E. et al., *World J Surg.* 24(8):942-951 (2000)). Therefore, preoperative molecular markers that could reliably stratify low-risk vs. high-risk patients would be useful in the initial surgical decision-making regarding the extent of thyroidectomy and the need for lymph node dissection.

We have used cDNA array analysis to identify candidate diagnostic and extent of disease markers in thyroid neoplasms that would be intermediate or suspicious on FNA cytology (Kebebew, E. et al., *Ann Surg.* 242(3):353-361; discussion 361-353 (2005); Kebebew, E. et al., *Surgery* in press (2005)). We found 6 novel candidate diagnostic and extent of disease markers of malignant thyroid neoplasms that were confirmed by reverse-transcriptase-polymerase-chain-reaction (RT-PCR); ECM1 (U68186, UniGene ID Hs.81071), TMPRSS4 (AF179224, UniGene ID Hs.161985), ANGPT2 (AF004327, UniGene ID Hs.583870), TIMP1 (NM_003254, UniGene ID Hs.522632), EFNB2 (L38734, UniGene ID Hs.149239) and EGFR (NM_005228, UniGene ID Hs.488293). In this study, we determine the diagnostic accuracy and the ability to predict disease aggressiveness using a multigene RT-PCR assay of these 6 novel candidate markers in combination.

BRIEF SUMMARY OF THE INVENTION

Approximately 30% of thyroid nodule fine needle aspiration (FNA) biopsies are indeterminate, nondiagnostic or suspicious. We used a real time quantitative reverse-transcriptase-polymerase-chain-reaction (RT-PCR) assay of 6 novel candidate diagnostic and extent of disease marker genes (ECM1, TMPRSS4, ANGPT2, TIMP1, EFNB2 and EGFR) in 126 thyroid tissues. To evaluate the performance of the scoring model for the diagnostic markers in combination, we determined the area under the receiver operating characteristic (ROC) curve (AUC). The level of ECM1, TMPRSS4, ANGPT2 and TIMP1 mRNA expression were independent diagnostic markers of malignant thyroid neoplasms. The AUC for the 4 diagnostic genes in combination was 0.993 with a sensitivity of 100%, a specificity of 94.6%, a positive predictive value of 96.5%, and a negative predictive value of 100%. In 31 thyroid nodule FNA biopsy samples, the scoring model had a sensitivity of 91.0%, a specificity of 95.0%, a positive predictive value of 92.9%, and a negative predictive value of 92.3%. The multigene assay correctly classified 93% of tumors into the correct risk group (low-risk vs. high-risk) with a sensitivity of 78.9% (true positive in high-risk tumors), specificity of 92% (true negative in low-risk tumors), positive predictive value of 87.5% and negative predictive value of 92%. In 11 malignant thyroid nodule FNA samples, the extent of disease scoring model correctly identified 3 of 4 high-risk differentiated thyroid cancers and 7 of 7 low-risk differentiated thyroid cancers. These novel multigene assays are an excellent diagnostic and extent of disease marker for differentiated thyroid cancer and would be a helpful adjunct to FNA biopsy of thyroid nodules.

BRIEF DESCRIPTION OF THE DRAWINGS

MACIS score categories: I=<6.0 (N=49), II=6.0 to 6.99 (N=5), III=7.0 to 7.99 (N=3), IV=$\geqq$8.0 (N=0).

EORTC score categories: I=<50 (N=39), II=50 to 65 (N=9), III=66 to 83 (N=8), IV=84 to 108 (N=1), and V=$\geqq$109 (N=0).

Error bars represent one standard deviation.

DETAILED DESCRIPTION OF THE INVENTION

Introduction

The present invention has identified six genes that show differential expression in benign and malignant thyroid neoplasms. RT-PCR was used to confirm the cDNA array expression data and results showed that the six genes are novel candidate diagnostic and extent of disease markers. To further determine the accuracy of these markers, the investigators used a multigene PCR-based assay composed of the six genes to analyze thyroid tissue and FNA biopsy samples from 126 patients. The gene expression levels were normalized and a logistic regression scoring model based on area under the curve (AUC) was used to evaluate the sensitivity, specificity, positive- and negative-predictive values of the six diagnostic genes. AUC of 1.0 represents a "perfect" diagnostic test without any false negative and false positive results.

Of the six genes, four genes are independent diagnostic markers for distinguishing benign from malignant thyroid neoplasms in 95 thyroid tissue samples (ECM1, TMPRSS4, ANGPT2 and TIMP1). The combination of these four markers provides greater predictive value than any individual marker alone. The AUC for the four diagnostic genes was 0.993, with a sensitivity of 100%, a specificity of 94.6%, and a positive predictive value of 96.5% and a negative predictive value of 100%. The accuracy of these markers were further validated by comparing the predicted malignancy using the scoring model to known histological diagnoses in 31 thyroid nodule FNA biopsy samples. Moreover, the multigene assay had a higher accuracy than FNA biopsy for distinguish noncancerous from cancerous thyroid tumors.

Furthermore, three genes in the set are useful markers for determining the stage of the thyroid cancer and segregating low-risk vs. high-risk differentiated thyroid cancers according to the TNM staging system and AMES risk classification system, respectively (ECM1, EFNB2 and EGFR). These marker genes correctly classified 93% of tumors into the correct risk group with a sensitivity of 78.9%, specificity of 92.0%, positive predictive value of 87.5%, and negative predictive value of 92.0%.

The invention also comprises a multigene diagnostic kit, composed of the six markers that can be used, optionally in combination with FNA cytology, to improve the diagnostic accuracy of determining if a thyroid nodule is cancerous, selecting the best treatment approach and predicting thyroid cancer patient outcome.

In one embodiment, the invention provides a method of diagnosing thyroid cancer in a subject, the method comprising the steps of contacting a biological sample from the subject with reagents that specifically bind to a panel of biomarkers comprising ECM1, TMPRSS4, ANGPT2, and T1MP1, and determining whether or not the marker is differentially expressed in the sample; thereby providing a diagnosis for thyroid cancer. The biomarker panel may further comprises EFNB2 and EGFR.

In another embodiment, the invention provides a method of determining the stage of thyroid cancer in a subject, the method comprising the steps of contacting a biological sample from the subject with reagents that specifically bind to a panel of biomarkers comprising ECM1, EFNB2 and EGFR, and determining whether or not the marker is differentially expressed in the sample; thereby staging the thyroid cancer. The biomarker panel may further comprises EFNB2 and EGFR.

In a third embodiment, the invention provides a method of distinguishing low risk and high risk differentiated thyroid cancers in a subject, the method comprising the steps of contacting a biological sample from the subject with reagents that specifically bind to a panel of biomarkers comprising ECM1, EFNB2 and EGFR, and determining whether or not the marker is differentially expressed in the sample, thereby determining the risk associated with the thyroid cancer. Alternatively, the biomarker panel may further comprise TMPRSS4, ANGPT2, and T1MP1.

In another embodiment, the invention provides a kit comprising reagents that specifically bind to a panel of biomarkers comprising one or more of ECM1, TMPRSS4, ANGPT2, T1MP1, EFNB2 and EGFR. This kit may comprise amplification of said biomarkers from a biological sample. The kit may further comprise (Q)RT-PCR, a microarray, or a cocktail of antibodies.

The present invention also provides methods of identifying a compound for treating or preventing thyroid cancer. In one embodiment, the method comprises the steps of: contacting a compound with a protein biomarker selected from ECM1, TMPRSS4, ANGPT2, T1MP1, EFNB2 and EGFR and detecting altered expression as compared to a control, thereby identifying a compound. In certain embodiments, the compound is a small molecule, polynucleotide, or peptide. In other embodiments, the assay is performed in vivo, in a cell, or in a tissue sample. In yet other embodiments, the assay is a biochemical assay performed in vitro. Assays particularly suited for use in conjunction with the present invention are well known in the art.

In yet another embodiment, the present invention provides therapeutic molecules for the treatment or prevention of thyroid cancer. In one embodiment, the therapeutic molecules comprise antibodies or immunogenic fragments of antibodies. In other embodiments, the molecules comprise antisense oligonucleotides, siRNAs, microRNAs, or other nucleic acids or nucleic acid analogues well known in the art. In particular embodiments, the therapeutic molecules specifically hybridize or immunogenically bind to a biomarker selected from ECM1, TMPRSS4, ANGPT2, T1MP1, EFNB2 and EGFR.

DEFINITIONS

A malignant thyroid neoplasm or thyroid cancer refers to all types of thyroid cancers, including e.g., papillary, follicular, medullary, hurthle cell and anaplastic cancers.

Other forms of cancer include carcinomas, sarcomas, adenocarcinomas, lymphomas, leukemias, etc., including solid and lymphoid cancers, head and neck cancer, e.g., oral cavity, pharyngeal and tongue cancer, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma.

The term "marker" refers to a molecule (typically protein, nucleic acid, carbohydrate, or lipid) that is expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, such markers are molecules that are overexpressed in a melanoma or other cancer cell in comparison to a non-cancer cell, for instance, 1-fold overexpression, 2-fold overexpression, 3-fold overexpression or more in comparison to a normal cell. Further, a marker can be a molecule that is inappropriately synthesized in the cancer cell, for instance, a molecule that contains deletions, additions or mutations in comparison to the molecule expressed on a non-cancer cell. Alternatively, such biomarkers are molecules that are underexpressed in a cancer cell in comparison to a non-cancer cell, for instance, 1-fold underexpression, 2-fold underexpression, 3-fold underexpression, or more. Further, a marker can be a molecule that is inappropriately synthesized in cancer, for instance, a molecule that contains deletions, additions or mutations in comparison to the molecule expressed on a non-cancer cell.

It will be understood by the skilled artisan that markers may be used in combination with other markers or tests for any of the uses, e.g., prediction, diagnosis, or prognosis of cancer, disclosed herein.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, thyroid tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., thyroid etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "overexpress," "overexpression" or "overexpressed" interchangeably refer to a protein or nucleic acid (RNA) that is transcribed or translated at a detectably greater level, usually in a cancer cell, in comparison to a non-cancer cell. The term includes overexpression due to transcription, post transcriptional processing, translation, post-translational processing, cellular localization (e.g., organelle, cytoplasm, nucleus, cell surface), and RNA and protein stability, as compared to a non-cancer cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a non-cancer cell. In certain instances, overexpression is 1-fold, 2-fold, 3-fold, 4-fold or more higher levels of transcription or translation in comparison to a non-cancer cell.

The terms "underexpress," "underexpression" or "underexpressed" or "downregulated" interchangeably refer to a protein or nucleic acid that is transcribed or translated at a detectably lower level in a cancer cell, in comparison to a non-cancer cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer patient, in comparison to a patient without cancer, in the context of the present invention.

"Therapeutic treatment" and "cancer therapies" refers to chemotherapy, hormonal therapy, radiotherapy, immunotherapy, and biologic (targeted) therapy.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length. The biomarkers described herein can be detected with probes that have, e.g., more than 70% identity over a specified region, or more than 80% identity, or more than 90% identity to the reference sequence provided by the accession number, up to 100% identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=-4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point $(T_m)$ for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The nucleic acids of the differentially expressed genes of this invention or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, such as the differentially expressed genes of the present invention, often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects" in the context of assays for testing compounds that modulate a marker protein includes the determination of a parameter that is indirectly or directly under the influence of a biomarker of the invention, e.g., a chemical or phenotypic. A functional effect therefore includes ligand binding activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, β-gal, GFP and the like), e.g., via chemiluminescence, fluorescence, calorimetric reactions, antibody binding, inducible markers, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists. Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing cancer biomarkers in vitro, in cells, or cell extracts, applying putative modulator compounds, and then determining the functional effects on activity, as described above.

Samples or assays comprising cancer biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of cancer biomarkers is achieved when the activity value relative to the control is about 80%, preferably 50%, more preferably 25-0%. Activation of cancer biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Predictive, Diagnostic, and Prognostic Methods

The present invention provides methods of predicting, diagnosing or providing prognosis of thyroid cancer by detecting the expression of markers differentially expressed in thyroid cancer. Prediction and diagnosis involve determining the level of a panel of thyroid cancer biomarker polynucleotide or the corresponding polypeptides in a patient or patient sample and then comparing the level to a baseline or range. Typically, the baseline value is representative of levels of the polynucleotide or nucleic acid in a healthy person not suffering from, or destined to develop, thyroid cancer, as measured using a biological sample such as a thyroid biopsy or a sample of a bodily fluid. Variation of levels of a polynucleotide or corresponding polypeptides of the invention from the baseline range (either up or down) indicates that the patient has an increased risk of developing thyroid cancer or an increased risk of its recurrence. For distinguishing between malignant and benign thyroid neoplasms, a panel of four or more markers is used: ECM1, TMPRSS4, ANGPT2, and T1PM1. For determining the stage of the cancer and distinguishing low risk vs. high risk differentiated thyroid cancers (according to the TNM staging system and AMES risk classification system, respectively), a panel of three or more markers is used: ECM1, EFNB2, and EGFR.

As used herein, the term "diagnosis" refers to distinguishing between malignant and benign thyroid neoplasms. As used herein, the term "providing a prognosis" refers to providing a prediction of the probable course and outcome of the thyroid cancer.

Antibody reagents can be used in assays to detect expression levels of the biomarkers of the invention in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis*, 18:2184-93 (1997); Bao, *J. Chromatogr. B. Biomed. Sci.*, 699:463-80 (1997). Liposome immunoassays, such as flow-injection liposome immunoassays and liposome immunosensors, are also suitable for use in the present invention. See, e.g., Rongen et al., *J. Immunol. Methods*, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, CA; Kit #449430) and can be performed using a Behring Nephelometer Analyzer (Fink et al., *J. Clin. Chem. Clin. Biochem.*, 27:261-276 (1989)).

Specific immunological binding of the antibody to nucleic acids can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.*, 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention. For in vivo imaging purposes, reagents that detect the presence of proteins encoded by cancer biomarkers, such as antibodies, may be labeled using an appropriate marker, such as a fluorescent marker.

Compositions, Kits and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Methods to Identify Compounds

A variety of methods may be used to identify compounds that prevent or treat thyroid cancer. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of a biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487-493 (1991) and Houghton et al., *Nature*, 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA*, 90:6909-6913 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217-9218 (1992)), analogous organic syntheses of small compound libraries (Chen et al., *J. Amer. Chem. Soc.*, 116:2661 (1994)), oligocarbamates (Cho et al., *Science*, 261:1303 (1993)), and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds is possible using the integrated systems of the invention.

Methods to Inhibit Marker Protein Expression Using Nucleic Acids

A variety of nucleic acids, such as antisense nucleic acids, siRNAs or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA, microRNA, or ribozyme oligonucleotides, phosphorothioate oligonucleotides can be used. Modifications of the phosphodiester linkage as well as of the heterocycle or the sugar may provide an increase in efficiency. Phophorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Xtreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-y-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, microRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, microRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

The following examples are offered to illustrate, but not to limit the claimed invention.

Methods

Thyroid Tissue and Fine Needle Biopsy Samples

Thyroid tissue samples, and clinical and histopathology data were obtained for 126 patients with informed consent: 95 frozen thyroid tumors and 31 thyroid FNA samples. The study was approved by the Committee on Human Research at the University of California, San Francisco.

Frozen thyroid tissue samples from patients with hyperplastic nodule (n=19), follicular adenoma (n=19), follicular thyroid cancer (n=19), follicular variant of papillary thyroid cancer (n=19), and papillary thyroid cancer (n=19) were studied. All thyroid tissue diagnoses were confirmed by permanent histology. The tissues used in our experiments were snap frozen in liquid nitrogen at the time of thyroidectomy and stored at −80° C. until total RNA was extracted.

In 31 patients undergoing thyroidectomy for thyroid nodules, a biopsy of the thyroid nodule was performed with a 25 gauge needle at the time of thyroidectomy with 4 passes through the nodule. The biopsy samples were immediately stored on ice until RNA extraction. These samples were evaluated as "unknown" to determine the feasibility of gene expression analysis and validate the diagnostic and extent of disease multigene assay scoring model. The AMES, AGES, MACIS and EORTC risk classification systems were used to categorize low-risk vs. high-risk tumors (Brierley, J. D. et al., *Cancer.* 79(12):2414-2423 (1997); Sanders, L. E. et al., *Arch Surg.* 133(4):419-425 (1998); Dean, D. S. et al., *Cancer Control.* 7(3):229-239 (2000)).

Real Time Quantitative RT-PCR

Total RNA was prepared by TRIZOL extraction (Invitrogen, Carlsbad, Calif.). One hundred and twenty-five nanograms of total RNA was reverse transcribed using the RT script cDNA synthesis kit (USB Corporation, Cleveland, Ohio). Real time quantitative RT-PCR was used to measure mRNA expression levels normalized to β-glucoronidase (GUS) mRNA expression. Normalized gene expression level=2−($C_t$ of gene of interest−$C_t$ of GUS)×100%, where $C_t$ is the PCR cycle threshold (Kebebew, E. et al., *Ann Surg.* 242(3):353-361; discussion 361-353 (2005); Kebebew, E. et al., *Surgery* 138(6):979-84; discussion 984-5. (2005); Ginzinger, D. G. *Exp Hematol.* 30(6):503-512 (2002)). The PCR primers and probes for the genes were purchased from Applied Biosystems (Assay-on-Demand Kit®, Foster City, Calif.).

All PCR reactions were performed in a final volume of 20 µl on an ABI PRISM®7900 Sequence Detection System (Applied Biosystems) with 1 µl cDNA template. The PCR condition was 95° C. for 12 minutes followed by 40 cycles of 95° C. for 15 seconds and 60° C. for 1 minute. All quantitative RT-PCR reactions were done in duplicate and repeated at least twice.

Statistical Analysis

We used logistic regression analysis to develop a diagnostic and extent of disease scoring model. To evaluate the performance of the logistic regression scoring model for normalized gene expression levels as diagnostic markers of malignant thyroid neoplasms, we determined the area under the receiver operating characteristic (ROC) curve (AUC). Associations between variables were determined by the Spearman Rank correlation test. A p value <0.05 was considered statistically significant.

Results

Figure 1:
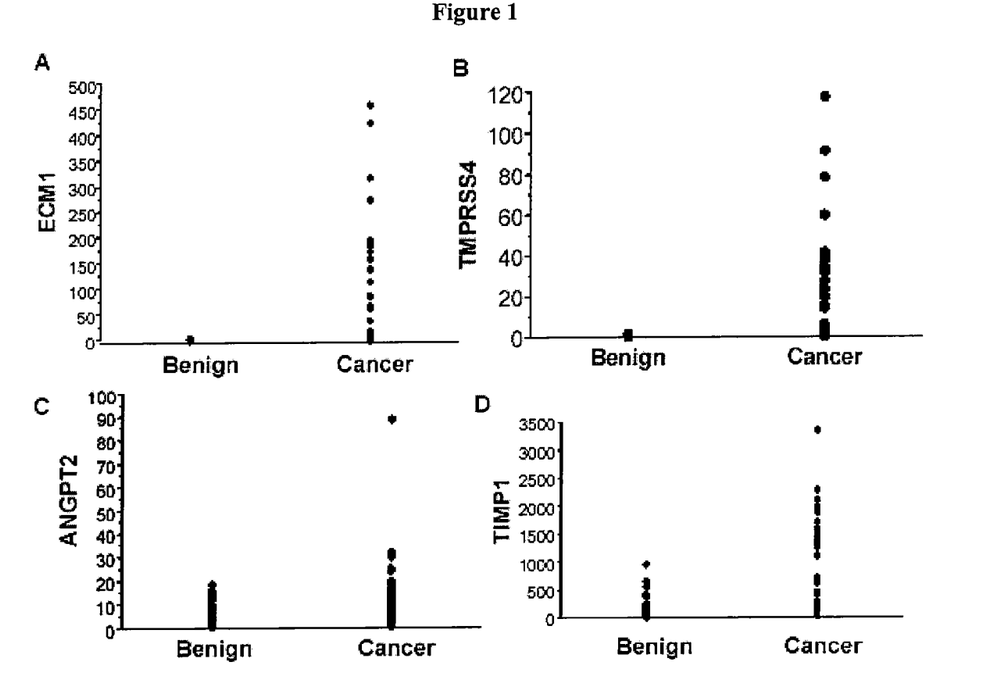
FIG. 1. Scatterplot of normalized ECM1, TMPRSS4, ANGPT2 and TIMP1 mRNA expression in benign (n=38) and malignant (n=57) thyroid neoplasms. All four genes were significantly upregulated in malignant tumors (p<0.0001 for ECM1, p<0.0001 for TMPRSS4, p=0.0085 for ANGPT2, and p=0.0010 for TIMP1 by Mann-Whitney Rank Sum test).
Figure 2:
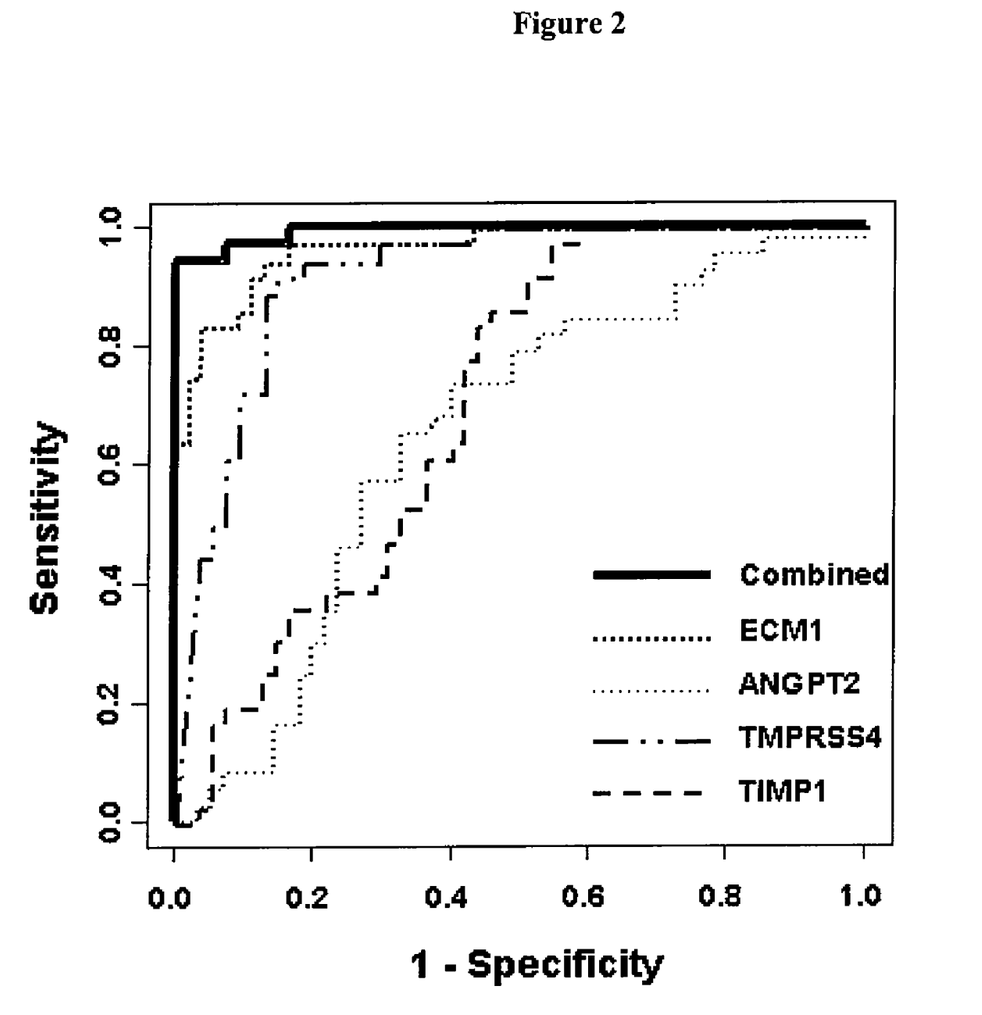
FIG. 2. ROC curve of normalized ECM1, TMPRSS4, ANGPT2 and TIMP1 mRNA expression in 95 patients with benign (n=38) and malignant (n=57) thyroid neoplasms. The combined use of the four markers had an AUC of 0.993 and was more accurate than one marker alone. AUC of 1.0 represents a "perfect" diagnostic test without any false negative and false positive results.

Diagnostic Accuracy of ECM1, TMPRSS4, ANGPT2 and TIMP1 mRNA Gene Expression Analysis in Thyroid Neoplasms We found normalized ECM1, TMPRSS4, ANGPT2 and TIMP1 mRNA expression were upregulated in malignant thyroid neoplasms, and were independent markers of malignant thyroid neoplasms by logistic regression analysis in 95 patients with benign (n=38) and malignant (n=57) thyroid neoplasms (FIG. 1). The scoring model was total score=4.800+7.774*log(ECM1+0.001)+1.979*log(TMPRSS4+0.001)+1.171*log(ANGPT2+0.001)−1.297*log(TIMP1+0.001) with a cutoff point of 0.00, so that when the score was >0.00, the case would be considered malignant. To evaluate the performance of the logistic regression scoring model for these 4 genes as diagnostic markers of malignant thyroid neoplasms, we determined the AUC. The AUC was 0.993 with a sensitivity of 100%, specificity of 94.6%, positive predictive value of 96.5%, and negative predictive value of 100% (FIG. 2). The AUC was highest for the 4 genes in combination: 0.966 for ECM1, 0.920 for TMPRSS4, 0.664 for ANGPT2, 0.705 for TIMP1, and 0.993 in combination. There was excellent correlation of ECM1, TMPRSS4, ANGPT2, and TIMP1 mRNA expression, normalized to GUS mRNA expression, between experiments ($R^2$=0.892-0.928, p<0.0001)

Validation of Diagnostic Scoring Model for ECM1, TMPRSS4, ANGPT2 and TIMP1 mRNA Expression Analysis in Thyroid Nodule FNA Samples The accuracy of the logistic regression scoring model for normalized ECM1, TMPRSS4, ANGPT2 and TIMP1 mRNA expression in combination cutoff levels to distinguish malignant from benign thyroid neoplasms was determined in patients with known benign and malignant thyroid histologic diagnoses in frozen thyroid tissue specimens. We therefore evaluated the diagnostic accuracy of normalized ECM1, TMPRSS4, ANGPT2 and TIMP1 mRNA expression levels in 31 thyroid nodule FNA samples obtained at the time of thyroidectomy (Table 1). In these samples, the model had a sensitivity of 91.0%, a specificity of 95.0%, a positive predictive value of 92.9%, and a negative predictive value of 92.3%.

Figure 3:
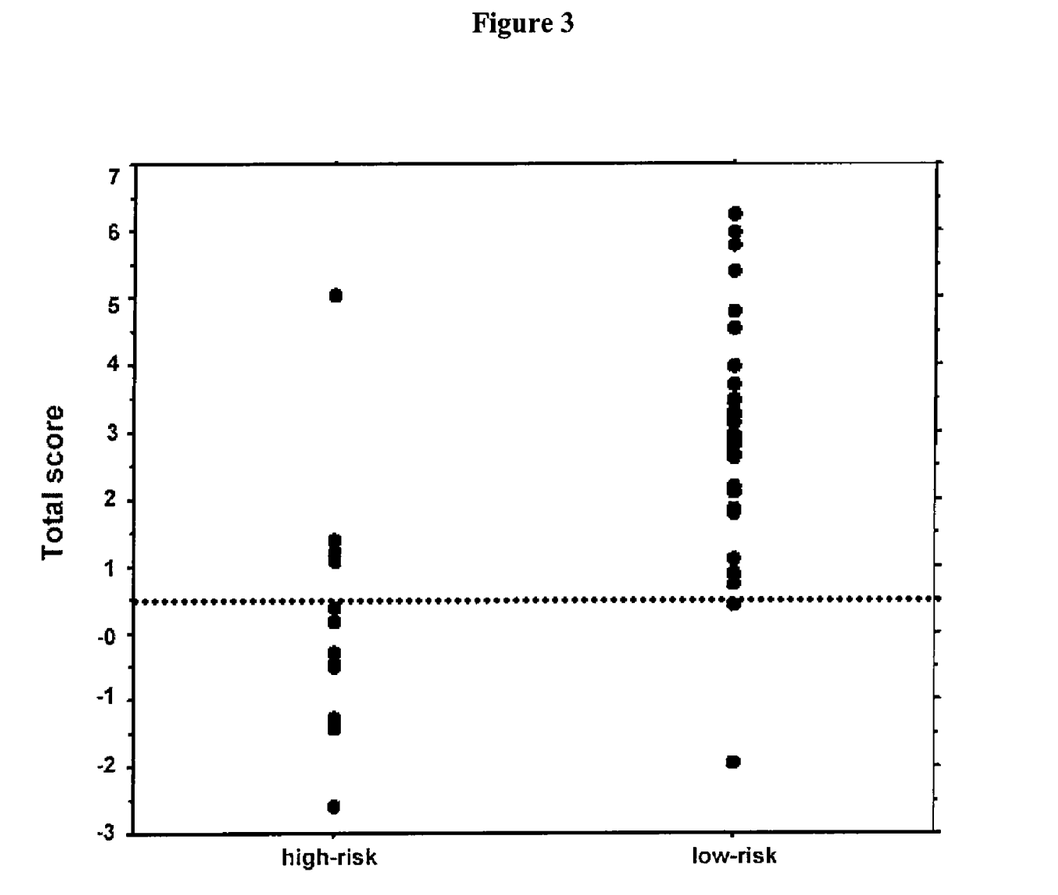
FIG. 3. Scatterplot of the total score for the scoring model for ECM1, EFNB2 and EGFR to distinguish AMES low-risk vs. high-risk differentiated thyroid cancers.
Figure 4:
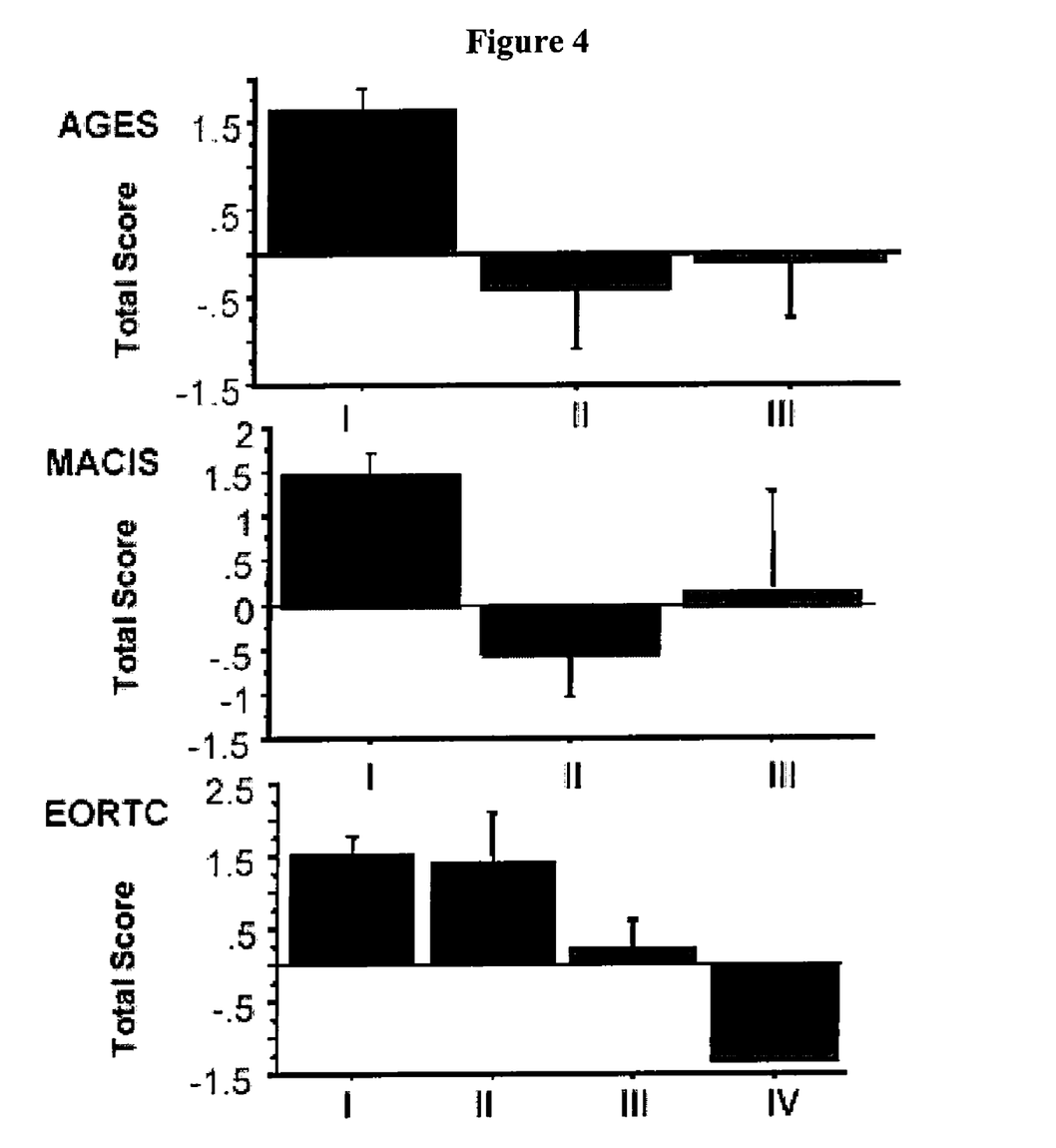
FIG. 4. Comparison of the total score for ECM1, EFNB2 and EGFR mRNA expression levels by AGES, MACIS and EORTC staging systems. There was a significant correlation in the total score for ECM1, EFNB2 and EGFR mRNA expression levels and the AGES (p=0.0176), MACIS (p=0.0174), and EORTC (p=0.044) staging systems. AGES score categories: I=$\leqq$3.99 (N=47), II=4.0 to 4.99 (N=5), III=5.0 to 5.99 (N=5), IV$\geqq$6.0 (N=0).

Normalized ECM1, EGFR and EFNB2 mRNA Expression Correlate with and Predict Extent of Disease in Differentiated Thyroid Cancer To determine the predictive value of measuring ECM1, EGFR and EFNB2 mRNA expression levels to stratify low-risk vs. high-risk differentiated thyroid cancer, we used logistic regression analysis. The scoring model was total score=6.43+1.03*log(ECM1+0.001)−2.60*log(EFNB2+0.001)−0.98*log(EGFR+0.001). A cutoff of 0.50 classified 93% of the differentiated thyroid cancer into the correct AMES risk group (FIG. 3). A total score cutoff of 0.50 had a sensitivity of 78.9% (true positive in high-risk tumors), a specificity of 92% (true negative in low-risk tumors), a positive predictive value of 87.5% and a negative predictive value of 92%. We also compared the combination of ECM1, EFNB2 and EGFR expression total score with the AGES, MACIS and EORTC staging systems. We found the total score model for these 3 genes in combination correlated with the AGES, MACIS and EORTC staging systems (FIG. 4). In 11 malignant thyroid nodule FNA samples, this scoring model correctly identified 3 of 4 high-risk differentiated thyroid cancers and 7 of 7 low-risk differentiated thyroid cancers.

Discussion

Our study focused mainly on thyroid nodules (20 follicular thyroid cancers, 22 follicular adenoma, 22 follicular variant of papillary thyroid cancer, 27 hyperplastic nodules) that are difficult to diagnose as benign or malignant by preoperative FNA cytology (Greaves et al. Cancer. 90(6):335-341 (2000); Baloch, Z. W. et al., Diagn Cytopathol. 26(1):41-44 (2002); Baloch, Z. W. et al., Am J Clin Pathol. 118(2):165-166 (2002)). Using a real time quantitative RT-PCR multigene assay of novel diagnostic markers for differentiated thyroid cancer, we were able to distinguish between benign and malignant thyroid neoplasms with a high accuracy. Furthermore, this multigene assay which included 3 markers of extent of disease was useful for segregating low-risk versus high-risk (AMES system) differentiated thyroid cancers and correlated with other staging systems (AGES, MACIS, EORTC).

The incidence of thyroid cancer has increased over the last three decades. Similarly, the incidence of thyroid nodules has increased as a result of greater use of more sensitive imaging studies (Silver, R. J. et al., Surg Clin North Am. 84(3):907-919 (2004)). Because of this changing epidemiology in thyroid neoplasm; a greater number of patients require FNA biopsy to exclude a diagnosis of thyroid cancer. Unfortunately, FNA biopsy is indeterminate or suspicious in a significant number of cases and results in over 100,000 diagnostic thyroidectomies being performed annually in the United States (Supit, E. et al., South Med J. 95(5):514-519 (2002); Caplan, R. H. et al., Am J Manag Care. 6(10):1134-1140 (2000)). Although there have been numerous studies evaluating potential diagnostic markers of thyroid cancer, most have had little clinical utility in tumors that would be indeterminate or suspicious on FNA cytology (Bojunga, J. et al., Clin Endocrinol (Oxf). 61(5): 523-530 (2004); Rosai, J. Tumori. 89(5):517-519 (2003)). We had previously identified 4 novel diagnostic markers of thyroid neoplasm that would be indeterminate or suspicious on FNA biopsy (Kebebew, E. et al., Ann Surg. 242(3):353-361; discussion 361-353 (2005); Kebebew, E. et al., Surgery in press (2005)). In this study, we demonstrate high accuracy of a real time quantitative RT-PCR multigene assay for distinguishing benign from malignant thyroid neoplasm in frozen thyroid tumor and thyroid FNA biopsy samples. These results could have important implications because they may reduce the number of diagnostic thyroidectomy performed and allow more complete initial surgical treatment.

The diagnostic accuracy of the real time quantitative RT-PCR multigene assay depends on the reproducibility of the gene expression levels, we therefore compared the inter-assay variability and found the results were reproducible with excellent correlation in normalized gene expression levels between experiments. Because the multigene assay scoring model was determined in frozen thyroid tissue with known histologic diagnoses, a bias may have been introduced in measuring the accuracy because of the lack of blinding to the thyroid tissue histology. Furthermore, the feasibility of performing the multigene assay in FNA biopsy samples was unknown. For these reasons, we confirmed the feasibility and validated the multigene assay scoring model in 31 thyroid nodule FNA biopsy. This suggests that the real time quantitative RT-PCR multigene assay could be implemented in the clinical setting.

The real time quantitative RT-PCR multigene assay also includes 3 genes that correlate with the extent or aggressiveness of differentiated thyroid cancer according to the TNM staging system and AMES risk classification system (Kebebew, E. et al., Ann Surg. 242(3):353-361; discussion 361-353 (2005); Kebebew, E. et al., Surgery 138(6):979-84; discussion 984-5. (2005)). We demonstrate that the multigene assay performs well for segregating low-risk versus high-risk tumors when analyzed in combination and in FNA biopsy samples. The optimal extent of thyroidectomy and need for prophylactic versus therapeutic lymph node dissection for differentiated thyroid cancer is controversial because there have been no reliable preoperative criteria for determining which patients have low-risk vs. high-risk disease, thus warranting aggressive or limited surgical intervention. In this context, the multigene assay may be helpful for predicting which patients have low-risk vs. high-risk tumors and help select the appropriate initial surgical treatment as well as adjuvant treatment as has been used for patients with neuroblastoma and more recently in breast cancer (Spitz, R. et al, Eur J Cancer. 40(18):2753-2759 (2004); Paik, S. et al., N Engl J Med. 351(27):2817-2826 (2004)).

In summary, our finding suggests that the real time quantitative RT-PCR multigene assay of 6 novel genes is an excellent diagnostic and extent of disease marker for differentiated thyroid cancer and would be a helpful adjunct to FNA biopsy of thyroid nodules.

TABLE 1

Comparison of ECM1, TMPRSS4, ANGPT2, and TIMP1 gene expression scoring model results in FNA biopsy results and permanent histologic diagnosis.

| FNA BIOPSY | SCORING MODEL RESULT | FINAL HISTOLOGY |
| --- | --- | --- |
| 5 BENIGN | 5 benign | 5 BENIGN |
| | | 3 thyroiditis |
| | | 2 normal |
| 15 INDETERMINATE | 11 BENIGN | 11 BENIGN |
| | (1 false negative) | 8 hyperplastic nodules |
| | 4 malignant | 3 follicular adenomas |
| | (1 false positive) | 4 malignant |
| | | 3 follicular variant of papillary thyroid cancer |
| | | 1 follicular thyroid cancer |
| 11 malignant | 1 benign | 11 malignant |
| | (false negative) | 11 papillary thyroid |
| | 10 malignant | cancer |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of distinguishing benign from malignant thyroid neoplasm in a subject, the method comprising the steps of:
   (a) contacting a thyroid tissue sample from the subject with reagents that specifically bind to a panel of biomarkers comprising ECM1, TMPRSS4, ANGPT2, and TIMP1, and (b) determining whether the normalized level of expression of each of said biomarkers in the panel is upregulated in the sample, thereby diagnosing malignant thyroid neoplasm.

2. The method of claim 1, wherein the reagents are nucleic acids.

3. The method of claim 1, wherein the reagents are oligonucleotides.

4. The method of claim 1, wherein the reagents are an RT PCR primer set.

5. The method of claim 1, wherein the sample is a fine needle aspiration biopsy.

6. The method of claim 1, wherein the biomarker panel further comprises EFNB2 and EGFR.

* * * * *